(12) United States Patent
Berger et al.

(10) Patent No.: US 7,427,588 B2
(45) Date of Patent: Sep. 23, 2008

(54) ETHER SULFONATE SURFACTANTS AND PROCESS FOR MAKING SAME

(76) Inventors: Paul Daniel Berger, 3014 Deer Creek Dr., Sugar Land, TX (US) 77478; Christie Huimin Berger, 3014 Deer Creek Dr., Sugar Land, TX (US) 77478

( * ) Notice: Subject to any disclaimer, the term of this patent is extended or adjusted under 35 U.S.C. 154(b) by 0 days.

(21) Appl. No.: 11/653,005

(22) Filed: Jan. 12, 2007

(65) Prior Publication Data

US 2008/0171895 A1    Jul. 17, 2008

(51) Int. Cl.
C07C 381/00    (2006.01)
C07C 143/42    (2006.01)

(52) U.S. Cl. ............... 510/424; 562/110; 260/512; 260/513; 260/612; 260/613

(58) Field of Classification Search ............ 510/424; 562/110; 260/512
See application file for complete search history.

(56) References Cited

U.S. PATENT DOCUMENTS

| | | | | |
|---|---|---|---|---|
| 2,535,677 | A | * | 12/1950 | Hollander et al. ........... 562/111 |
| 3,424,693 | A | | 1/1969 | Stein al. |
| 3,424,694 | A | | 1/1969 | Stein et al. |
| 4,091,014 | A | * | 5/1978 | Johnson et al. ............. 562/42 |
| 4,138,345 | A | * | 2/1979 | Williams ................. 507/246 |
| 4,267,123 | A | | 5/1981 | Chen et al. |
| 4,293,428 | A | * | 10/1981 | Gale et al. ................ 507/238 |
| 4,733,728 | A | | 3/1988 | Morita et al. |
| 4,842,776 | A | * | 6/1989 | Schmidt et al. ............. 562/42 |
| 5,069,817 | A | | 12/1991 | Schmid et al. |
| 5,075,042 | A | | 12/1991 | Allison et al. |
| 5,523,471 | A | * | 6/1996 | Delpy et al. .............. 562/110 |
| 6,063,733 | A | | 5/2000 | Berger et al. |
| 6,121,200 | A | | 9/2000 | Berger et al. |

FOREIGN PATENT DOCUMENTS

JP    2005161524 A    *    6/2005

OTHER PUBLICATIONS

Preparation and properties of Surfactant ether sulphonates. Pueschel, Fritz; Kraatz, Karl Heinz Zentralinst, Org. Chem, DAW, Berlin, Ger. Dem. Rep. Abhadlngen der Akademie der Wissenschaften der DDR (1997), 1976.*
(1978) John Wiley and Sons, N.Y. Rosen, Surfactants and Interfacial Phenomena.
Linfield, Anionic Surfactants, Part II, Surfactant Science Series vol. 7 (1976) p. 345-380 Marcel Decker, N.Y.
Schramm, Surfactants-Fundamentals and Applications in the Petroleum Industry (2000) p. 206-216 Cambridge University Press, Cambridge UK.
Lucassen-Reynders, Anionic Surfactants, Physical Chemistry of Surfactant Action (1981) Marcel Decker, N.Y.
Stache—Anionic Surfactants-Organic Chemistry vol. 56. Surfactants Science Series, (1995) Marcel Decker, N.Y.
McCutcheon's Emulsifiers and Detergents (2001) McPublishing Co. Glen Rock, NJ.
Basf Alkyl Ether Sulfonates Product Brochure 2002.

* cited by examiner

Primary Examiner—Mark Eashoo
Assistant Examiner—Mohammad Reza Asdjodi

(57) ABSTRACT

Novel compositions of matter and the process of preparing these surfactants having the structure:

$$R^1[-(O-(R^2O)_m-(R^3O)_n-(R^4)]_y$$

where:
$R^1$=alkyl, alkenyl, amine, alkylamine, dialkylamine, trialkylamine, aromatic, polyaromatic, cycloalkane, cycloalkene,
$R^2$=$C_2H_4$ or $C_3H_6$ or $C_4H_8$,
$R^3$=$C_2H_4$ or $C_3H_6$ or $C_4H_8$,
$R^4$=linear or branched $C_7H_{14}SO_3X$ to $C_{30}H_{60}SO_3X$ when y=1,
$R^4$=linear or branched $C_7H_{14}SO_3X$ to $C_{30}H_{60}SO_3X$ or H when y>1 but at least one $R^4$ must be linear or branched $C_7H_{14}SO_3X$ to $C_{30}H_{60}SO_3X$,
$m \geq 1$,
$n \geq 0$,
n+m=1 to 30+,
$y \geq 1$,
X=alkali metal or alkaline earth metal or ammonium or amine.

These novel ether sulfonate surfactants have excellent surfactant properties making them suitable for a variety of applications as surfactants including agriculture, adhesives, coatings, deinking, detergents, emulsion polymerization, laundry, lubricants, metal working, mining, oilfield, personal care, pharmaceuticals, and soil remediation.

3 Claims, No Drawings

ETHER SULFONATE SURFACTANTS AND PROCESS FOR MAKING SAME

CROSS REFERENCE TO RELATED APPLICATIONS

Not Applicable

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of surfactants and more specifically to novel ether sulfonate surfactants, a process for making same, and applications for their use.

Surfactants are used for a wide variety of applications because their unique structures impart special properties to systems containing them. These properties include the ability to allow immiscible liquids such as oil and water to mix, to improve the wetting properties of a liquid on a solid, to allow solids to be suspended in liquids, and to foam liquids. It is for these reasons that surfactants find widespread use in many industries including, but not limited to, agriculture, adhesives, coatings, deinking, detergents, emulsion polymerization, laundry, lubricants, metal working, mining, oilfield, personal care, pharmaceuticals, and soil remediation.

Surfactants can be divided into four main classes by the charges they carry. The four classes are (1) nonionic surfactants having no charge, (2) anionic surfactants having a negative charge, (3) cationic surfactants having a positive charge, and (4) amphoteric surfactants having positive, negative or no charge depending on the pH of the system in which the surfactant is contained. The properties associated with the different types of surfactants are described in many articles and books including Rosen, *Surfactants and Interfacial Phenomena*, (1978). A compilation of most of the surfactants available along with their properties and a list of their manufacturers is available from *McCutcheon's Emulsifiers and Detergents* (2001).

Of the four classes of surfactants, anionic surfactants are found to have the most widespread uses and are produced in the largest volume. This is primarily due to their lower cost, better performance, and because of the applications where they are used such as laundry, personal care, household, institutional and industrial cleaning, agriculture and coatings, that tend to require large volumes of lower cost material made from readily available raw materials. The anionic surfactants are essentially various sulfates, sulfonates, phosphates, phosphonates, and carboxylates. The chemistry of these products is very well described in *Anionic Surfactants-Organic Chemistry, Volume* 56, Surfactant Science Series, Marcel Dekker (1995). Their physical properties are addressed in *Anionic Surfactants-Physical Chemistry of Surfactant Action, Volume* 11, Surfactant Science Series. Marcel Dekker (1981). The most common and widely used anionic surfactants are the sulfates and the sulfonates. These include alcohol sulfates, alcohol ether sulfates, glycerol sulfates, alkoxylated alkylphenol sulfates and sulfonates, alkylaryl sulfonates, alpha-olefin sulfonates, alkane sulfonates, and sulfosuccinates. Sulfonates are generally more thermally and hydrolytically stable then sulfates since the sulfur group is attached directly to a carbon. In sulfates, the sulfur group is attached to the carbon through an oxygen group. Thus sulfates can be considered esters of sulfuric acid and the hydrolysable ester bond makes them relative instability. This instability limits the conditions and applications where they can be used.

Ether sulfates contain not only a sulfate ester but also various amounts of ethylene, propylene, or butylene oxide, or mixtures of two or more of these. Due to the presence of additional hydrophilic alkyl oxides, the ether sulfates in general are more tolerant to electrolytes and divalent metal ions and are therefore useful where hard waters are encountered. Unfortunately the ether sulfates are also hydrolytically unstable and their uses are limited where high temperature or extreme pH conditions (high or low) are encountered.

One solution to this instability problem is to employ ether sulfonates. These surfactants are both salt tolerant and hydrolytically stable. Ether sulfonates have been reported to give excellent performance under conditions of high salinities, high temperatures and extreme pH conditions. Schwartz et al., *Surface Active Agents and Detergents*, Interscience Publishers, Vol. II p 74-75, refers to these desirable properties of ether sulfonates and discloses sulfonated polyethoxylated alkyl phenols and their method of preparation by reaction of an ethoxylated alkyl phenol with sodium ethanol sulfonate. In addition, Schwartz et al. discloses that ether-linked sulfonates may be prepared by the addition reaction of butane sultone with an alkyl phenol.

The prior art on the production of ether sulfonates is summarized below in Table 1 where:
R=alkyl, alkenyl, phenyl, alkenylphenyl, amine,
R'=$C_2H_4$, $C_3H_6$ or $C_4H_8$, or mixtures of 2 or more of these,
R"=an alkenyl spacer
M=alkali or alkaline metal, ammonium or an amine

TABLE 1

| | R—O—(R'O)$_n$—R"SO$_3$M | |
|---|---|---|
| Reference | n | R" |
| U.S. Pat. No. 5,075,042 | 1 to 30 | $C_2H_4$ |
| U.S. Pat. No. 3,424,693 | 0 | $C_8H_{16}$ to $C_{22}H_{44}$ |
| U.S. Pat. No. 4,138,345 | 1 to 10 | $C_3H_6$ or $C_4H_8$ |
| U.S. Pat. No. 4,267,123 | 1 to 13 | $C_2H_4$, $C_3H_6$, $C_4H_8$, or $CH_2(CH(OH))CH_2$ |
| U.S. Pat. No. 4,293,428 | 2 to 20 | $C_2H_4$ |
| U.S. Pat. No. 4,733,728 | 0 to 15 | $C_2H_4$, $C_3H_6$, or $CH_2(CH(OH))CH_2$ |
| This Invention | 1 to 30+ | $C_7H_{14}$ to $C_{30}H_{60}$ |

U.S. Pat. No. 5,075,042 issue to Allison et al. on Dec. 24, 1991 describes the preparation of aliphatic poly(ethyleneoxy) sulfonates by the chlorination with thionyl chloride of an ethoxylated aliphatic alcohol and subsequent conversion of the resulting chloride to the sulfonate with sodium sulfite. This patent goes on to reveal that certain aliphatic poly(ethyleneoxy)sulfonates are commercially available as AVANEL® S Anionic Surfactants.

BASF Corporation currently markets AVANEL® surfactants. Their literature describes alkyl ether sulfonates of C12-15 alkyl with 7 EO (AVANEL® S-70), with 15 EO (AVANEL® S-150 CG), and C8 alkyl with 3 EO (AVANEL® S-74) as "unique because the ethylene oxide gives certain nonionic characteristics to the products, and the sulfonate group provides certain anionic characteristics. These products are extremely stable over a wide range of pH and electrolyte concentrations." The key features of the alkyl ether sulfonates, as pointed out by BASF, include excellent hard water tolerance, hydrolytic stability over the entire pH range, biodegradability, oxidative stability in hypochlorite and oxygen bleaches, thermal stability, high electrolyte tolerance, excellent rinsability, sheeting action, extreme mildness to the skin, good emulsification characteristics, and low critical micelle concentrations.

U.S. Pat. Nos. 3,424,693 and 3,424,694 issued to Stein, et al. on Jan. 28, 1969 discloses the reaction of partially neutralized olefin sulfonic acids containing 8 to 22 carbon atoms with a sultone reactive product and the recovery of the resulting mixture of surface-active compounds. Both these patents claim yields of between 10 and 50 mole percent for the reaction product of the sultone and sultone reactive compound with the remainder being the neutralized salt of olefin sulfonic acid. Alkoxylated products are not disclosed as sultone reactive starting materials in this patent. Ether sulfonates of alkylamines have been prepared in the past. Williams in U.S. Pat. No. 4,138,345 issued on Feb. 6, 1979, discloses the reaction of the metallic salts of alkoxylated or dialkoxylated amines with propane or butane sultone. These give the corresponding mono and di sulfonates of the amines and these have been found useful alone or in combination with other surfactants in the recovery of oil.

U.S. Pat. No. 4,267,123 issued to Chen et al. on May 12, 1981 states that "propane sulfonates of various amines and polyethoxylated alcohols are known surfactants. However, propane sulfonates of alcohols and thiols have only been prepared in the literature by reaction of alkali metal salts of alcohols and thiols with propane sultone. This is a convenient high yield laboratory synthesis but is not desirable on a large scale for several reasons. Foremost among them are the fact that (1) such a reaction requires multistep synthesis and purification of propane sultone, (2) propane sultone is expensive to purify and its overall yield of 80-90% limits the yield in the preparation of the propane sulfonates and (3) propane sultone is a known carcinogen."

U.S. Pat. No. 4,293,428 issued to Gale, et al. on Oct. 6, 1981 involves the synthesis and application of alcohol ether sulfonates for oil recovery. This patent states that it has been determined that "positioning ethylene oxide and/or propylene oxide adjacent to the sulfonate group of a given surfactant tends to give it more water solubility and increases its tolerance to high concentrations of mono and di-valent salts". In addition the ether sulfonates were found to exhibit very good resistance to hydrolysis in high-temperature reservoirs. A thorough discussion of their application in oil recovery is given in *Surfactants—Fundamentals and Applications in the Petroleum Industry*, L. Schramm editor, Cambridge Press (2000) p 209-214.

U.S. Pat. No. 4,733,728 to Morita, et al. Mar. 29, 1988 describes alkylether sulfonates prepared from alkoxylated alcohol or alkylphenol by reacting with sodium isethionate, propane sultone, or epichlorohydrin followed by reacting with sodium sulfite. Our invention differs from the prior art in several ways. The presence of a long hydrocarbon chain spacer between the last alkylene oxide and the terminal sulfonate group gives the products of our invention greater oil solubility and lower irritation properties. Stein, et al in U.S. Pat. Nos. 3,424,693 and 3,424,694 also uses a long chain hydrocarbon spacer that is also derived from an olefin sulfonic acid. Stein et al. however, does not use alkoxylates, as we do, and therefore these materials do not have the high electrolyte tolerance or hardness tolerance of our compositions. Also, our process of reacting an un-neutralized olefin sulfonic acid with the alkoxide of an alkoxylated alcohol, phenol or amine gives yields of >90% whereas Stein, et al. only get 10 to 50 mole percent. Finally, our invention and process does not require the use of toxic reactants such as epichlorohydrin, thionyl chloride, propane sultone or butane sultone that are used by the other reference cited from the prior art. These important differences will become apparent through the examples presented.

BRIEF SUMMARY OF THE INVENTION

The primary object of the present invention is to make new ether sulfonates.

Another object of the present invention is to provide new ether sulfonates made from readily available and non-toxic materials.

Another objective of the present invention is to provide a new process to make the new ether sulfonates from readily available, non-toxic raw materials.

Another objective of the present invention is to provide new surfactants that have excellent surface tension lowering properties, interfacial tension lowering properties, low Critical Micelle Concentration (CMC), good wetting/foaming properties, and are thermally and hydrolytically stable.

Another object of the present invention is to provide new ether sulfonates that can be used in oilfield, agricultural, personal care, paint, adhesives, metal treating, lubrication, emulsion polymerization, detergent and laundry applications.

Other objects and advantages of the present invention will become apparent from the following descriptions, wherein, by way of illustration and example, an embodiment of the present invention is disclosed.

In accordance with a preferred embodiment of the invention, there is disclosed novel compositions of matter comprising ether sulfonate surfactants of the formula:

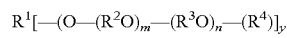

where:
  $R^1$=alkyl, alkenyl, amine, alkylamine, dialkylamine, trialkylamine, aromatic, polyaromatic, cycloalkane, cycloalkene, $R^2$=$C_2H_4$ or $C_3H_6$ or $C_4H_8$, $R^3$=$C_2H_4$ or $C_3H_6$ or $C_4H_8$, $R^4$=linear or branched $C_7H_{14}SO_3X$ to $C_{30}H_{60}$ $SO_3X$ when y=1, $R^4$=linear or branched $C_7H_{14}SO_3X$ to $C_{30}H_{60}$ $SO_3X$ or H when y>1 but at least one $R^4$ must be linear or branched $C_7H_{14}SO_3X$ to $C_{30}H_{60}$ $SO_3X$,
  $m \geq 1$,
  $n \geq 0$,
  n+m=1 to 30+,
  $y \geq 1$,
  X=alkali metal or alkaline earth metal or ammonium or amine.

When y is greater than 1 as would be the case if the starting $R^1$ is, for example, trimethylol propane, pentaerythritol, a diethanolamine, or triethanolamine all the terminal groups can be $C_7H_{14}SO_3X$ to $C_{30}H_{60}$ $SO_3X$ or some can be $C_7H_{14}SO_3X$ to $C_{30}H_{60}$ $SO_3X$ and some can be H as long as at least one is $C_7H_{14}SO_3X$ to $C_{30}H_{60}$ $SO_3X$.

In accordance with a preferred embodiment of the invention, there is disclosed a process for preparing novel ether sulfonates of the formula:

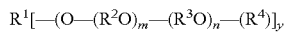

where

R$^1$, R$^2$, R$^3$, R$^4$, m, n, y have the same meaning as described above.

This product is made by reacting an olefin sulfonic acid with the metal alkoxide derivative of one or more from the group alkoxylated phenol, alkoxylated polyphenol, alkoxylated alkylphenol, alkoxylated polyalkylphenol, alkoxylated linear alcohol, alkoxylated branched alcohol, glycol, polyglycol, alkoxylated monoalkylamine, alkoxylated dialkylamine, monoalkanolamine, dialkanolamine, trialkanolamine.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

In accordance with the present invention, novel ether sulfonate surfactants are produced from the reaction of an olefin sulfonic acid and a metal alkoxide. Any molecule that can be oxyalkylated can be used as the starting material to produce the metal alkoxide. Examples of such include phenol, alkylphenol, alkoxylated phenol, alkoxylated alkylphenol, linear alcohol, alkoxylated linear alcohol, branched alcohol, alkoxylated branched alcohol, cyclic alkane, cyclic alkene, polyaromatic, glycol, polyglycol, amine, alkylamine, alkoxylated alkylamine, dialkylamine, alkoxylated dialkylamine, monoalkanolamine, dialkanolamine, trialkanolamine.

Olefin sulfonic acids can be linear or branched and from 7 carbons to over 30 carbons in length depending on the particular properties one wishes to impart to the final ether sulfonate. Longer chain length olefin sulfonic acids will give more hydrophobicity as will linear sulfonic acids compared to shorter and more branched olefin sulfonic acids. The preferred olefin sulfonic acid is C7 to C30+ olefin sulfonic acid prepared by the SO$_3$ sulfonation of a single alpha olefin or mixture of alpha-olefins containing from about 7 to 30 or more carbons. These sulfonic acids are commonly referred to as alpha-olefin sulfonic acids or AOS acids. The chemistry and procedures for producing AOS acid are well known to those familiar with the art. A comprehensive discussion of AOS chemistry can be found in Anionic Surfactants Part II, Surfactant Science Series, Marcel Dekker (1976), p 345-380.

Reaction temperatures can be between about ambient to about 200° C., depending on the olefin sulfonic acid and the hydroxyl containing starting material. More preferably temperatures are between 50° C. and 150° C. and most preferably temperatures are between 90° and 140° C.

The first step in the process is to start with or produce an oxyalkylated alcohol, amine, glycol, phenol, alkylphenol. The oxyalkylation reaction to produce the starting material is well known to those familiar with the art. After the oxyalkylate has been prepared or secured, it is converted to an alkali metal alkoxide. This is done by reacting the oxyalkylate with a strong base such as sodium hydroxide or potassium hydroxide, or a metal alcoholate such as potassium methylate or sodium methylate. When sodium or potassium hydroxide is used, the material is heated to remove water and form the sodium or potassium alkoxide. When sodium methylate or potassium methylate is used, the material is heated to remove methanol, again forming the sodium or potassium alkoxide. Other metal hydroxide and alcoholates may be used such as lithium hydroxide, magnesium hydroxide, calcium hydroxide or ethylates of the various metals however the hydroxides and methylates of sodium and potassium are preferred because of cost and availability.

An example of the series of reactions leading to the final product are shown below in reaction sequence A, starting with the addition of alkyl oxide (1), followed by the conversion to the metal alkoxide (2), and finally the reaction with olefin sulfonic acid (3) resulting in the final ether sulfonate product. The catalyst used in step (1) may be sodium or potassium hydroxide, or sodium or potassium methylate. This particular example shows the final product of reaction (3) having all terminal OH groups capped by an alkyl sulfonate group. When y is greater than 1, products can be made that have less than all the terminal OH groups capped by an alkylsulfonate group, if desired, as long as at least one OH has been capped.

Since sodium hydroxide, potassium hydroxide, and sodium methylate are commonly used as catalysts for oxyalkylation, these catalysts may be left un-neutralized after the completion of the initial oxyalkylation reaction and supplemented with additional sodium or potassium hydroxide or methylate to the required stoichiometric amount for the subsequent reaction with olefin sulfonic acid.

High concentrations of basic alkali metal catalyst are known to produce narrow distribution alkoxylates as is taught in U.S. Pat. No. 5,069,817 issued to Schmid, et al. on Dec. 3, 1991. The problem with the use of high levels of catalyst is that large quantities of salts are produced upon neutralization of these catalysts in order to remove them after the oxyalkylation has been completed causing a sludge that is difficult to remove. Since our invention uses the un-neutralized product from the oxyalkylation reaction, quantities up to stoichiometric amounts of sodium or potassium hydroxide or sodium or potassium methylate catalyst can be used in the oxyalkylation reaction to produce narrow distribution alkoxylates as shown in Sequence B, reaction 1a. Once the oxyalkylation is completed, olefin sulfonic acid can be added directly to the reactor to make the final product as shown in Sequence B, reaction 2a.

Narrow distribution alkoxylates are useful in producing narrow distribution ethersulfonates by the process of this invention. These narrow distribution ether sulfonates are useful in applications where a broad distribution may separate into its various homologues. An example is in recovering oil from a subterranean formation. The ethersulfonates having a broad distribution may chromatographically separate on the reservoir rock resulting in changes in performance as the surfactant propagates through the formation. Also narrow distribution products have been shown to have more defined solubilities since they contain less higher molecular weight material that may cause cloudiness as a result of reduced cloudpoints.

Reaction Sequence A

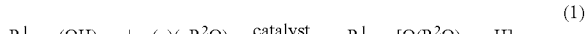

(1)

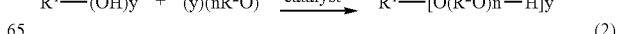

(2)

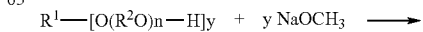

-continued

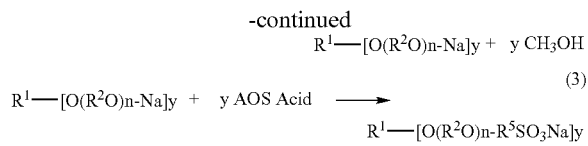

Reaction Sequence B for narrow distribution alkoxylation

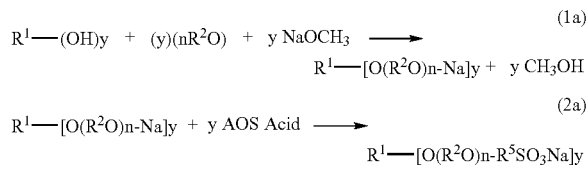

Where:
- $R^1$ is aromatic, cycloalkene, cycloalkane, amine, alkanolamine, dialkanol amine, alkylamine, alkoxylated alkyl amine, branched or linear alkane,
- $R^2 = C_2H_4$, $C_3H_6$, $C_4H_8$, or mixtures of two or more of these,
- n=1 to 30+,
- $y \geq 1$,
- $R^5$ = linear or branched $C_7H_{14}$ to $C_{30}H_{60}$, and
- the catalyst used in step (1) is sodium or potassium hydroxide or sodium or potassium methylate.

Since sodium hydroxide or potassium hydroxide or sodium methylate is usually used to convert the terminal alkoxy group to the corresponding sodium or potassium alkoxide, the final product will usually be in the sodium or potassium form. Exchanging the sodium or potassium with other mono, di or trivalent metals, ammonium or an amine can easily be accomplished and these techniques are well known to those familiar with the art.

Example 1 Preparation of Alcohol Ether Sulfonates

This example uses a C10-12 alcohol with 7 moles of Ethylene Oxide and 6 Moles of Propylene Oxide (Witconol™ 1206 from Akzo-Nobel), sodium methylate (Aldrich) and C12 AOS Acid (Bio-terge® AS-12 Acid from Stepan Company) to produce an alcohol ether sulfonate containing both Ethylene and Propylene Oxide groups.

92.6 (0.100 Mole) grams of C10-12 alcohol with 7 Moles EO and 6 Moles of PO are added to a 250 ml roundbottom flask equipped with a stirrer, temperature controller and reflux condenser. 21.6 (0.100 Mole) grams of sodium methylate (25% in methanol) is added and the mixture is heated to 130° C. while purging with a stream of Nitrogen. After all the methanol has been removed and collected (20.0 grams), 24.8 grams (0.100 Mole) of the C12 AOS Acid is added slowly to maintain the temperature at 130° C. and control the foaming of the reaction. The reaction is completed after 2 additional hours at 130° C. following the addition of the C12 AOS acid.

The final product was then analyzed for anionic surfactant, nonionic surfactant, free sulfonic acid and sulfuric acid. The amount of anionic surfactant was measured using a surfactant electrode and found to be 0.80 me/g. The theoretical activity is 0.84 me/g based on the equivalent weight of 1195. No nonionic surfactant (free alcohol alkoxylate) was found by gravimetric analysis after passing through a strong cationic ion-exchange resin column. No free sulfonic or sulfuric acid was found by potentiometric titration with hexylamine in isopropanol.

Example 2 Surface Properties of Alcohol Ether Sulfonate from Example 1

This example demonstrates the excellent surfactant properties of the compositions of the present invention.

Various surface properties were determined for the product from Example 1 to determine its suitability as a surfactant. All measurements were done at 24° C. unless noted otherwise.

The Draves wetting time of a 0.1% wt/wt distilled water solution of the product from Example 1 was found to be instantaneous.

The Surface Tension of a 0.1% w/wt solution of the product from Example 1 was found to be 34.2 mN/m.

The interfacial tension of a 0.1% in distilled water solution was measured against mineral oil and found to be 0.6 mN/m at 50° C.

The Critical Micelle Concentration (CMC) of the product from Example 1 was found to be 0.00001 moles/liter.

The foaming of a 0.5% w/w solution was measured by mixing 100 ml in a Waring Blender at high speed for 30 seconds and immediately pouring the resulting foam into a 1000 ml graduated cylinder. The initial foam height was 600 ml and the time for 50 ml of liquid to appear (half-life) was 3 minutes and 54 seconds.

These results indicate the product from Example 1 has excellent surfactant properties for use as a wetting agent, in lowering surface tension and interfacial tension, in producing low CMCs and as a foaming agent. These excellent surfactant properties makes this and similar products defined by our invention suitable for applications as surfactants in agriculture, adhesives, coatings, deinking, detergents, emulsion polymerization, laundry, lubricants, metal working, mining, oilfield, personal care, pharmaceuticals, and soil remediation.

Example 3 Preparation of a Nonylphenol Ethoxysulfonate 42.8 grams (0.108 Mole) of the 4 Mole ethoxylate of nonylphenol (Witconol™ NP-40 from Akzo-Nobel) were added to a 250 ml round bottom flask equipped with a stirrer, temperature controller and reflux condenser. 17.3 grams (0.108 Mole) of a 25% wt/wt solution of sodium hydroxide in methanol were added and the mixture heated to 130° C. while purging with Nitrogen to remove the methanol. After all the methanol was removed and collected (14.9 grams), 31.4 grams (0.108 Mole) of C14/16 AOS Acid (Akzo-Nobel) was added slowly to maintain the temperature and control the foaming. The reaction was continued for an additional 2 hours at 130° C. after completing the addition of the AOS Acid. Before removing the final product from the flask it was allowed to cool to below 90° C. and then diluted with an equal weight (76.7 grams) of water to give a 50% active solution by weight.

The final product was then analyzed for anionic surfactant, nonionic surfactant, free sulfonic acid and sulfuric acid. The amount of anionic surfactant measured using a surfactant electrode was found to be 0.68 me/g compared to a theoretical 0.71 me/g for the 50% active product, based on an equivalent weight of 708. No nonionic surfactant (free ethoxylated nonylphenol) was found by gravimetric analysis after passing through a strong cationic ion-exchange resin column. No free sulfonic or sulfuric acid was found by potentiometric titration with hexylamine in isopropanol.

Example 4 Preparation of Alkylamine Ether Di-Sulfonates 186.6 grams (0.200 Moles) of tallowamine ethoxylate with 15 Moles of EthyleneOxide (Crisomin™ T-15 from Clariant Corporation), were added to a 500-ml roundbottom flask equipped with a stirrer, temperature controller and reflux condenser. 86.4 grams (0.400 Moles) of a 25% by weight solution of sodium methylate in methanol were added and the mixture heated to 130° C. to remove and collect the methanol. After all the methanol (77.2 grams) was removed, 99.2 grams (0.400 Moles) of C12 AOS Acid (Bio-terge® AS-12 Acid from Stepan Company) was added slowly to maintain the temperature and control the foaming. The mixture was held at 130° C. for an additional 2 hours after the final addition of AOS Acid. The final product was then analyzed for anionic surfactant, nonionic surfactant, free sulfonic acid and sulfuric acid. The amount of anionic surfactant was found to be 1.30 me/g compared to a theoretical 1.35 me/g using an equivalent weight of 736 for the 100% active di-sulfonated monotallow ethoxylated amine. No nonionic surfactant (free tallow amine ethoxylate) was found by gravimetric analysis after passing through a strong cationic ion-exchange resin column. No free sulfonic or sulfuric acid was found by potentiometric titration with hexylamine in isopropanol.

Example 5 Pesticidal Composition Having Improved Performance

This example demonstrates the utility of the compositions of the present invention as non-irritating surfactants to enhance the efficacy of pesticidal formulations.

U.S. Pat. Nos. 6,603,733 issued on May 16, 2000 and 6,121,200 issued on Sep. 19, 2000, both to Berger, et al., describe the use of polyoxyalkylene alkylamine surfactants having reduced eye irritation by the addition of an effective amount of a sulfated polyoxyalkylene alkylphenol, alcohol sulfate, polyoxyalkylene alcohol sulfate, mono- or di-alcohol phosphate mono- or di-(polyoxyalkylene alcohol) phosphate, mono- or di-(polyoxyalkylene alkylphenol) phosphate, polyoxyalkylene alkylphenol carboxylate or polyoxyalkylene alcohol carboxylate surfactant. Examples of these surfactants are combined with glyphosate to give herbicidal compositions having reduced eye irritation and effective weed-killing properties.

Taking advantage of the excellent surfactant properties found in Example 2 above and the properties described in the literature for alkyl ether sulfonates in general, including excellent wetting, interfacial and surface tension lowering, extreme mildness to the skin, biodegradability and high electrolyte tolerance; the composition from Example 4 above was formulated into a glyphosate formulation as described in Example 16 of U.S. Pat. No. 6,121,200. The ethoxylated tallow amine ether sulfonate from Example 4 above was substituted for the combined polyethoxylated tallowamine and sulfated polyoxyethylene nonylphenol described in Example 16 of U.S. Pat. No. 6,121,200 to compare the performance of this single surfactant to the combined surfactant of U.S. Pat. No. 6,121,200.

Thus test material E was prepared by mixing 69.3 grams of glyphosate concentrate with 10.0 grams of the material from Example 4 above and 20.7 water and compared to test materials A, B, C and D from U.S. Pat. No. 6,121,200 where A is glyphosate containing 15.47 weight percent ethoxylated tallowamine along with 69.3 weight percent glyphosate, the remainder being water; B contains 15.49 weight percent of total surfactant, 69.3 weight percent glyphosate, the remainder being water and the surfactant being a mixture of 13.1 grams of ethoxylated tallowamine and 2.3 grams of sulfated polyoxyethylene nonylphenol, C contains 12.7 weight percent of this surfactant mixture along with 69.3 weight percent glyphosate, the remainder being water, and D contained 10.0 weight percent of the surfactant mixture, 69.3 wt percent glyphosate and the remainder being water.

Test material E was diluted with water to 0.5, 1.0, 2.0 and 4.0 weight percent glyphosate aqueous solutions and sprayed onto a test field containing rhizome Johnsongrass. Half the test plot was sprayed with water after 2 hours in order to tests the rainfastness of the formulation. The test plot was evaluated 7 and 14 days after treatment. Percent control of the Johnsongrass for test material E is shown below in Table 2 compared to the reported results for test material A, B, C, and D. An untreated check plot showed no control of the Johnsongrass.

TABLE 2

| Test Material | 0.5% 7 days | 0.5% 14 days | 1.0% 7 days | 1.0% 14 days | 2.0% 7 days | 2.0% 14 days | 4.0% 7 days | 4.0% 14 days |
|---|---|---|---|---|---|---|---|---|
| A | 42 | 82 | 62 | 99 | 67 | 100 | 88 | 100 |
| B | 57 | 90 | 75 | 99 | 68 | 99 | 88 | 100 |
| C | 42 | 97 | 70 | 99 | 73 | 100 | 88 | 100 |
| D | 47 | 95 | 58 | 99 | 73 | 99 | 83 | 100 |
| E | 50 | 95 | 70 | 100 | 75 | 100 | 90 | 100 |
| E Rainfast | 48 | 95 | 65 | 100 | 75 | 100 | 85 | 100 |

Example 6 Composition for Oil Recovery

This example demonstrates the utility of the compositions of the present invention as surfactants for oil recovery at high temperatures in the presence of high concentrations of electrolyte and divalent metal salts.

Anionic surfactants and surfactant mixtures have been used to recover oil from sub-terranean reservoirs by reducing the interfacial tension between and injection fluid containing surfactant and the oil trapped within the microscopic pores of the reservoir rock. Gale, et al. in U.S. Pat. No. 4,293,428, referred to previously, describes the use of alkoxylated alcohol ether sulfonates as surfactants having tolerance to high concentrations of electrolytes and divalent cations. The inventors stress the need to have a narrow distribution surfactant in order to minimize the chromatographic separation of the mixture when propagating through the reservoir.

An alkoxylated tridecanol was prepared by first reacting 6 moles (336 grams) of propylene oxide (PO) with 1 mole (200 grams) of branched tridecanol (Exxal® 13 from Exxon) using 1 mole (216 grams) of a 25% by weight methanolic solution of sodium methylate catalyst. The methanol from the catalyst (162 grams) was removed before the start of the propoxylation reaction. The propoxylation was followed by the addition of 6 moles (264 grams) of ethylene oxide (EO). After the ethoxylation was completed the nonionic was analyzed and found to have a Weight Average Molecular Weight ($MW_{wa}$) of 798 (800 theoretical). HPLC confirmed that the material had a narrow distribution.

Using a Waters HPLC the Number Average Molecular Weight ($MW_{na}$) was found to be 791. This gave a Dispersity Factor D of 1.01 where $D=MW_{wa}/MW_{na}$.

400 grams (0.500 Moles) of the sodium alkoxylate of the narrow distribution propoxylated/ethoxylated tridecanol was reacted with 124 grams (0.500 Moles) of C12 alpha-olefin sulfonic acid (Bio-terge® AS-12 Acid from Stepan Company) for 2 hours at 130° C. The final product was found to contain no residual nonionic propoxylated/ethoxylated tridecanol and had an anionic equivalent weight of 1039 grams/equivalent (1048 theoretical).

A solution of 0.10 weight percent of the final reaction product was prepared in a brine consisting of 10.0 wt percent NaCl, 2.00 weight percent $CaCl_2$ and 1.00 weight percent $MgCl_2$. The interfacial tension against a crude oil having an API Gravity of 18 was measured at 95° C. using a University of Texas Model 500 spinning drop tensiometer. The Interfacial tension was found to be 0.0012 mN/m.

Example 7 Evaluation of Alkyl Ether Sulfonates as Components of a Laundry Detergent This example demonstrates the utility of the compositions of the present invention as components of laundry detergents and cleaning compounds to replace mixtures of nonionic and anionic surfactants and also to replace aromatic anionic surfactants.

The sodium salt of a 5-6 mole ethoxylated C12-14 alcohol ether sulfonate was prepared from C14/16 AOS Acid and Witconol™ SN-70, both obtained from Akzo-Nobel, according to the procedure described in Example 1. Liquid laundry detergents of the formulations shown in Table 3 were prepared. All values are expressed as weight percent. Witconate™ 1260 is a 60% active by weight sodium linear dodecylbenzene sulfonate. Witconol™ SN-70 is a $C_{12}$ to $C_{14}$ alcohol with approximately 5.4 Moles of ethylene oxide.

TABLE 3

|  | Formulation A | Formulation B |
| --- | --- | --- |
| Witconate ™ 1260 Slurry | 17.0 | — |
| Witconol ™ SN-70 | 40.0 | — |
| SN-70/C14-16 AOS Acid(50% Aqueous) | — | 60.0 |
| Tinopal ™ CBS (Ciba) | 0.1 | 0.1 |
| Ethanol | 7.0 | — |

TABLE 3-continued

|  | Formulation A | Formulation B |
| --- | --- | --- |
| Triethanolamine | 5.0 | — |
| Water | 30.9 | 39.9 |

Detergency was measured by visually inspecting naturally soiled fabrics according to ASTM D 2960. Both formulations gave acceptable and comparable results on cotton, polyester and mixed cotton/polyester fabrics.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A process for preparing ether sulfonates of the formula:

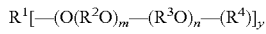

where:
$R^1$=alkyl, alkenyl, amine, alkylamine, dialkylamine, trialkylamine, aromatic, polyaromatic, cycloalkane, cycloalkene,
$R^2$=$C_2H_4$ or $C_3H_6$ or $C_4H_8$,
$R^3$=$C_2H_4$ or $C_3H_6$ or $C_4H_8$,
$R^4$=linear or branched $C_7H_{14}SO_3X$ to $C_{30}H_{60}SO_3X$ when y=1,
$R^4$=linear or branched $C_7H_{14}SO_3X$ to $C_{30}H_{60}SO_3X$ or H when y>1 but at least one $R^4$ must be linear or branched $C_7H_{14}SO_3X$ to $C_{30}H_{60}SO_3X$,
m≧1,
n≧0,
n+m=1 to 30+,
y≧1,
X=alkali metal or alkaline earth metal or ammonium or amine,
where:
an olefin sulfonic acid is reacted with the metal alkoxide of one or more from the group alkoxylated phenol, alkoxylated polyphenol, alkoxylated alkylphenol, alkoxylated polyalkylphenol, alkoxylated linear alcohol, alkoxylated branched alcohol, glycol, polyglycol, alkoxylated monoalkylamine, alkoxylated dialkylamine, monoalkanolamine, dialkanolamine, trialkanolamine.

2. The process described in claim 1 where the olefin sulfonic acid is linear or branched C7 to C30+ olefin sulfonic acid prepared by the $SO_3$ sulfonation of an alpha-olefin.

3. The process described in claim 1 where the metal alkoxide is sodium or potassium alkoxide.

* * * * *